United States Patent
Williams et al.

(10) Patent No.: US 7,041,121 B1
(45) Date of Patent: May 9, 2006

(54) APPARATUS FOR TREATING PROSTATE CANCER AND METHOD FOR SAME

(75) Inventors: Stephen J. Williams, Danville, CA (US); James G. Lovewell, San Leandro, CA (US); Thomas H. McGaffigan, Saratoga, CA (US)

(73) Assignee: Medtronicvidamed, Inc., Minneapolis, MN (US)

( * ) Notice: Subject to any disclaimer, the term of this patent is extended or adjusted under 35 U.S.C. 154(b) by 183 days.

(21) Appl. No.: 10/356,226

(22) Filed: Jan. 31, 2003
(Under 37 CFR 1.47)

Related U.S. Application Data

(60) Provisional application No. 60/353,816, filed on Jan. 31, 2002.

(51) Int. Cl.
*A61N 5/067* (2006.01)
*A61N 5/01* (2006.01)

(52) U.S. Cl. .............................. 607/89; 607/88; 606/15

(58) Field of Classification Search ............. 607/88–90, 607/92, 93; 604/19–21; 606/15
See application file for complete search history.

(56) References Cited

U.S. PATENT DOCUMENTS

| | | | | |
|---|---|---|---|---|
| 5,445,608 | A * | 8/1995 | Chen et al. | 604/20 |
| 5,514,669 | A * | 5/1996 | Selman | 514/63 |
| 5,705,518 | A * | 1/1998 | Richter et al. | 514/410 |
| 5,964,756 | A | 10/1999 | McGaffigan et al. | |
| 6,454,791 | B1 * | 9/2002 | Prescott | 607/89 |
| 6,602,274 | B1 * | 8/2003 | Chen | 607/88 |
| 6,624,187 | B1 * | 9/2003 | Pandey et al. | 514/410 |
| 2003/0167033 | A1 * | 9/2003 | Chen et al. | 604/20 |
| 2003/0212052 | A1 * | 11/2003 | Kessel et al. | 514/171 |

OTHER PUBLICATIONS

"Drugs Approved by the FDA," http://www.centerwatch-.com/patient/drugs/dru387.html, CenterWatch, Inc., 1 page (last printed Jan. 30, 2002).

"Axcan Scandipharm Products & Services," http://www.axcanscandipharm.com/products/photofrin_pl.html, Axcan Scandipharm Inc., 19 pages (last printed Jan. 30, 2002).

"Photofrin Approved in Finland for Advanced and Esophageal Cancer," http://www.pslgroup.com/dg/e88ca.htm, Doctor's Guide Global Edition, 2 pages (last printed Jan. 31, 2003).

"Drugs & Herbs," http://my.webmd.com/content/drugs/3/4046_6533?bn=Photofrin, WebMDHealth, 4 pages (last printed Jan. 31, 2003).

(Continued)

*Primary Examiner*—Roy D. Gibson
(74) *Attorney, Agent, or Firm*—Shumaker & Sieffert, P.A.

(57) ABSTRACT

A medical device for photodynamically treating cancerous tissue, such as prostate cancer, comprising a body, a needle extendable from the body and at least one light-emitting (e.g., laser) diode mounted on the needle. The body is sized and configured for introduction into the urethra of a patient. The needle is movable between a retracted position housed substantially within the cylindrical body, and a deployed position in which the needle extends from the cylindrical body to enable it to penetrate into prostate tissue. The light-emitting diode is adapted to emit light to activate a photosensitizing agent (e.g., porfimer sodium) in or adjacent cancerous tissue in the prostate. Methods of treating cancer and other embodiments of medical devices for cancer treatment are also disclosed.

20 Claims, 1 Drawing Sheet

OTHER PUBLICATIONS

"Drugs Approved by the FDA," http://www.centerwatch.com/patient/drugs/dru387.html, CenterWatch, Inc., 2 pages (last printed Jan. 31, 2003).

"Product Label, " http://www.accessdata.fda.gov/scripts/cder/onctools/labels.cfm?GN=porfimer+sodium, U.S. Food and Drug Administration, 14 pages (last printed Jan. 31, 2003).

"Photofrin Receives Approval for Lung Cancer in Canada," http://www.docguide.com/dg.nsf/PrintPrint/5BC9B4C34CDAEBE4852567B00068A2B1, Doctor's Guide to the Internet, 2 pages (last printed Jan. 31, 2003).

"Axcan Files Canadian Submission for PHOTOFRIN for High Grade Dysplasia Associated to Barrett's Esophagus Priority Review Status Granted," http://www1.newswire.ca/releases/July2001/12/c1716.html, 3 pages (last printed Jan. 31, 2003).

Gagel, M., "Photodynamic Therapy with Porphyrins," http://www.derm.ubc.ca/laser/pdt.html, Derm Web at UBC, 4 pages (last printed Jan. 31, 2003).

"Photodynamic Therapy: Overview," http://www.cchse.org/chapters/BC%20Lower%20Mainland/BCLM%20Feb1%20Speakers°. . . , PHOTOFRIN®: Year 1 U.S. Experience, 1 page (last printed Jan. 31, 2003).

"Photodynamic therapy with Photofrin II induces programmed cell death in carcinoma cell lines," http://www.omlc.ogi.edu/pubs/abs/he94.html, 1 page (last printed Jan. 31, 2003).

"PDT Physician Information," http://www.di medinc.c m/pdt/pdt%20physici n.htm, 2 pages (last printed Jan. 31, 2003).

"Diomed 603nm PDT Laser," http://www.di medinc.c m/pdt/630pdt.htm, 2 pages (last printed Jan. 31, 2003).

"PDT Disposables," http://www.di medinc.c m/pdt/disp s bles.htm, 2 pages (last printed Jan. 31, 2003).

"LumaCare Non Coherent . . . The Future of PDT," http://www.lum c re.c m/, 2 pages (last printed Jan. 31, 2003).

"New Device Approval Diomed 630 PDT Laser Model T2USA—P990021," http://www.fd .g v/cdrh/md /d cs/p990021.html, CDRH Consumer Information, 2 pages (last printed Jan. 31, 2003).

* cited by examiner

APPARATUS FOR TREATING PROSTATE CANCER AND METHOD FOR SAME

RELATED APPLICATION

This application claims priority on U.S. provisional application Ser. No. 60/353,816, filed Jan. 31, 2002. The foregoing U.S. provisional application is incorporated herein by reference in its entirety.

BACKGROUND OF THE INVENTION

1. Field

This invention relates generally to medical devices and methods for treating cancer, and to exemplary embodiments of such devices and methods for treatment of prostate cancer.

2. Background

Porfimer sodium, sold by Axcan Scandipharm Inc. of Birmingham, Ala., under the trade designation "Photofrin," is a photosensitizing agent used in the photodynamic therapy of tumors and is currently used for treating cancer in a body of a patient. After injection into the body of a patient, Photofrin is light-activated, for example by illumination with 630 nanometer wavelength laser light. In the current applications, the drug is activated by a light-emitting device exterior of the body.

SUMMARY OF THE INVENTION

Exemplary embodiments of the invention include methods and medical devices useful to treat prostate cancer with a photosensitizing agent, such as porfimer sodium (e.g., "Photofrin"), and a medical device having a probe provided with one or more light-emitting elements or devices.

In general, the Photofrin drug is introduced under the invention into a portion of the body, for example the tissue of the prostate, by means of the probe or otherwise. The probe is then used to supply light to the tissue in the vicinity of the drug, and preferably the tissue in which the drug is located, to activate or stimulate the Photofrin drug.

More specifically, the Photofrin can be introduced intravenously into the body like a transfusion. For example, the drug can be injected into the arm or put into a major vein so that it can circulate throughout the body. When treating the prostate, for example prostate cancer, however, only the portion of the drug in the portion of the prostate intended to be treated is activated. Since cancer cells tend to require more blood than other slower growing tissue, the Photofrin drug concentrates more in the cancerous tissue than in other noncancerous tissue. Alternatively, or in addition, a smaller amount of the drug can be injected into the prostate by means of a needle.

Whether the drug is introduced into the whole body, whether intravenously or otherwise, or delivered only to a specific area of the body, a light-emitting probe is then introduced into the body to activate the drug in such specific or targeted area of the body. In one method of the invention where it is desired to treat the prostate, the drug can be activated transurethrally in the prostate.

A preferred exemplary embodiment of a method of the invention generally comprises: (a) introducing into the body a photosensitizing agent that in response to absorbing light creates or increases an activity to destroy or inhibit cancerous tissue; (b) introducing a medical probe having a distal portion into the body such that the distal portion is in the vicinity of the cancerous tissue; and (c) supplying light from the distal portion of the medical probe to activate the photosensitizing agent so that it emits sufficient energy to destroy or inhibit cancerous tissue.

Examples of light-responsive activities of the photosensitizing agent that may destroy or inhibit cancerous tissue include: emitting energy; emitting of energy at a different wavelength than the absorbed light; inducing a photochemical effect; inducing a thermal effect; and eliciting a necrotic reaction and associated inflammatory response. It is believed that "Photofrin" is marketing as exhibiting a photochemical effect, and eliciting a necrotic reaction and associated inflammatory response, but this application is not limited to any theory of the operation of the photosensitizing agent.

Any suitable medical device can be used to activate the Photofrin drug within the body. One suitable device can be similar to the TUNA device being sold by Vidamed, Inc. as modified to provide at least one laser diode on the one or more needles of such device. One embodiment of such Vidamed TUNA device, prior to modification, is disclosed in U.S. Pat. No. 5,964,756 issued Oct. 12, 1999, which is incorporated herein by reference.

A preferred exemplary embodiment of a medical device of the invention generally comprises a body, a needle extendable from the body and at least one light-emitting (e.g., laser) diode mounted on the needle. The body is sized and configured for introduction into the urethra of a patient. The needle is movable between a retracted position housed substantially within the cylindrical body, and a deployed position in which the needle extends from the cylindrical body to enable it to penetrate into prostate tissue. The light-emitting diode is adapted to emit light to activate a photosensitizing agent (e.g., porfimer sodium) in or adjacent cancerous tissue in the prostate. A method of treating cancer is also disclosed.

DETAILED DESCRIPTION OF EXEMPLARY EMBODIMENTS

Figure 1:
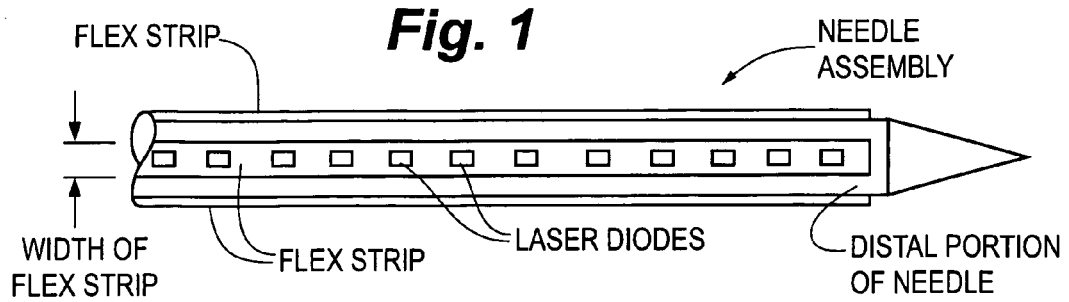
FIG. 1 is a side view of a portion of an exemplary embodiment of a needle assembly of the invention.
Figure 2:
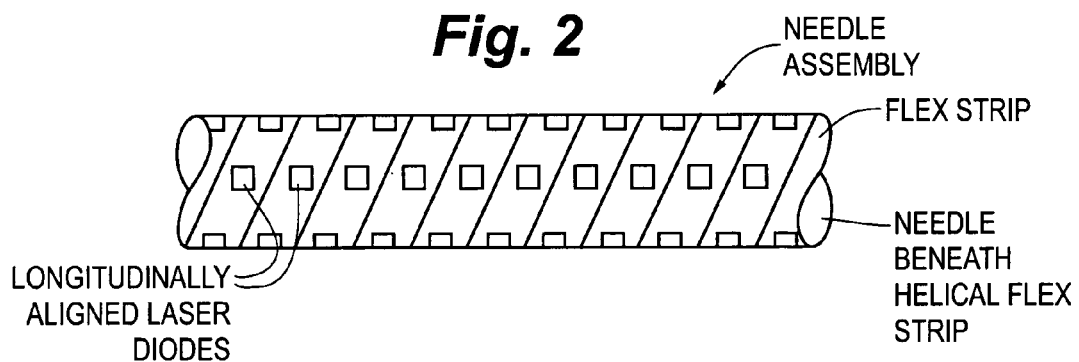
FIG. 2 is a partial side view of another exemplary embodiment of a needle assembly of the invention.
Figure 3:
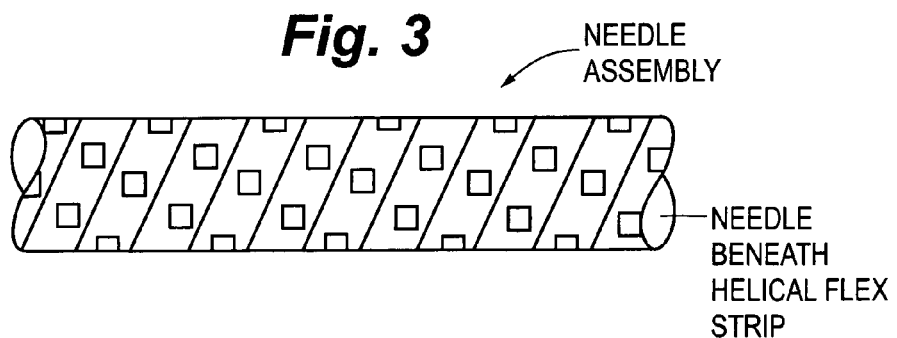
FIG. 3 is a partial side view of yet another exemplary embodiment of a needle assembly of the invention.

In one embodiment of a modified Vidamed device, light-emitting semiconductor laser diodes are mounted on the outside of one or more needles. Several versions of such a needle are shown in FIGS. 1–3, each of which shows one or more flex strips mounted to the exterior of the needle. Each of the flex strips contains at least one and as shown a plurality of spaced-apart laser diodes thereon. In the embodiment of FIG. 1, at least one such flex strip is mounted to the outer cylindrical surface of a needle by any suitable means such as an adhesive or heat shrinking. The needle can be of any suitable type such as bendable needle made from any suitable material such as stainless steel or a shape memory alloy. The needle can be solid or have one or more central lumens extending longitudinally therethrough for supplying a liquid to the targeted tissue and/or for containing sensors or electrical leads. The needle assembly of FIG. 1 has a plurality of four flex strips mounted longitudinally along at least a distal portion of the needle, each of the flex strips being circumferentially spaced apart around the needle. Three of such flex strips are visible, the fourth flex strip being on the backside of the needle. As such, each of the flex strips extends parallel with the needle.

Where the needle assembly is required to be bent, for example through an angle of approximately 90° for extending through the urethral wall into the tissue of the prostate, as is done with current needle electrode devices being sold by Vidamed, it is desirable that the entire needle assembly be flexible. In this regard, the flex strip can be appropriately sized so as to bend with the needle through such deflection angle. For example, it is preferable to provide a relatively small width for each of the flex strips, that is the flex strips are narrow relative to the diameter of the needle, so as to facilitate the bending thereof.

FIGS. 2 and 3 show a segment of a distal portion of a needle assembly having a flex strip mounted helically around the needle. The needle and flex circuit in FIGS. 2 and 3 can each be similar in construction to the needle and flex circuit discussed above with respect to FIG. 1, and the flex circuit can be mounted to the needle in any suitable manner such as discussed above. Although shown as a single flex strip, it should be appreciated that a plurality of flex strips extending end-to-end can be provided. Each of the flex strips is provided with at least one and as shown a plurality of laser diodes extending along the length of the flex strip in longitudinally spaced-apart positions. The laser diodes are longitudinally aligned in the needle assembly of FIG. 2 and staggered in the needle assembly of FIG. 3. It should be appreciated that any suitable configuration of laser diodes can be provided, but the staggering of the laser diodes as in FIG. 3 may facilitate bending of the needle assembly. Likewise, the helical arrangement of the flex circuit on the needle facilitates such bending, particularly for angles as large as 90°. Specifically, such helically disposed flex circuit inhibit buckling of the flex circuit.

As can be seen, in each of the embodiments disclosed in FIGS. 1–3, the laser diodes are prepositioned on a flex circuit and the flex circuit is then wrapped around or otherwise placed on a flexible central member, such as a needle. The whole flex circuit chip assembly is then covered with a protective coating (not shown), such as heat shrinkable tubing, to provide a smooth surface and to encapsulate and water proof the underlying semiconductor devices.

Other configurations or laser diodes and needles are within the scope of the invention. For example, one or more semiconductor laser dyes can be placed in a mold and then encapsulated. Such assembly can be encapsulated directly onto the needle or thereafter mounted on the needle in any suitable manner.

The semiconductor laser diodes can be electronically coupled in a series parallel combination. Some of the diodes are in series so they carry an equal amount of current, but to keep the voltage levels reasonable a series parallel combination is desirable. In addition, a number of the diodes can be wired in series so that the voltage does not get too high and a number of parallel circuits provided so that the current does not get too high. The conductors for the semiconductor laser devices can include a central conductor passing down a longitudinal lumen in the needle which serves as one of the two conductors required to supply power to the laser diodes. In a flex circuit arrangement, however, both conductors for the laser diodes can be included on the flex circuit.

As discussed above, the laser diodes can be placed along any length of the distal portion of the needle or other central member. For needles utilized for treating the prostate, the length of the distal portion of the needle having laser diodes thereon would be a function of the transverse measurement of the prostate. In one preferred embodiment of the device that is adaptable for treating different sized prostates, an effective needle length of at least 22 millimeters would be provided with laser diodes thereon.

Figure 4:
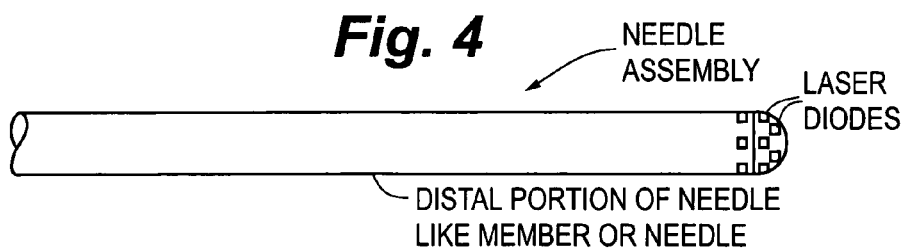
FIG. 4 is a partial side view of yet another exemplary embodiment of a needle assembly of the invention.

The embodiment disclosed in FIG. 4 shows a needle or other introduceable central member having laser diodes mounted only on the distal portion of the member. The diodes can be molded into an encapsulating material and then mounted on the introducing member, mounted on the introducing member by an adhesive or mounted on the introducing member by any other suitable means. The laser diodes can be electrically coupled together so that any one or more of the laser diodes can be selectively activated.

The one or more needles of such modified device are introduced transurethrally into the tissue of the prostate and, more specifically, into the targeted tissue of the prostate. Once the laser diodes or other light-emitting devices are desirably positioned in the prostate in the vicinity of the targeted tissue, for example close to the cancerous tumor, the diodes are energized so as to cause laser light to activate the Photofrin drug in the tumor or other targeted tissue. Where the Photofrin drug has been introduced intravenously into the prostate tissue, the drug resides in the blood stream of the tumor. Where the drug has been injected into the prostate tissue, for example by a needle, the drug is dispersed in the tissue of the prostate. The precise placement of the laser diodes in the prostate permits more precise targeting of tissue for treatment. Tissue not exposed to laser light is not treated.

In one preferred method of the invention for treating targeted tissue, such as cancerous tissue in the prostate, electrical energy is focused to the laser diodes positioned where high concentrations of the cancer are located. The series of parallel series combinations discussed above are advantageous in this regard as the operator of the device can switch power to different parallel banks to focus the device to the tissue areas having high cancer concentration. Hence, the number of laser diodes being activated, and the amount of energy being supplied to such electrodes, can be controlled. For example, one parallel bank of laser diodes may be at the head or distal end of the needle. Alternatively, one may focus energy along the sides or the length of the needle. One may deploy a needle having laser diodes extending along 22 millimeters of the distal portion of the needle, but only activate the distal ten millimeters of the needle. The procedure can be performed with ultrasound monitoring to facilitate location of the targeted tissue and supply of the drug and light energy thereto.

In another method of the invention, energy can be supplied to one or more of the light-emitting diodes during introduction of the needle into the targeted tissue. For example, it is believed that prostate cancer is spread in specific areas like pepper, that is prostate cancer is not merely a centralized mass. Where it is desired to attack or treat such cancerous regions, one can activate the light-emitting diodes during deployment of the needle in order to treat the particular region that the device is traveling through.

Hence, one method is to insert the needle to a fixed location in the targeted tissue and then activate the LEDs. Such location would probably be determined by ultrasound, or some other monitoring means, and be in the location of the cancer. Another treatment procedure would involve inserting the device part of the way into body tissue, and then activating the device as it continues its travel through the tissue.

It should be appreciated that other light-emitting probes can be provided and be within the scope of the present invention. For example, a probe having a light-carrying fiber optic element extending to a distal end of an introduceable member can be provided. In one such embodiment, the fiber optic element is disposed in a longitudinal lumen of an introducer needle.

Thus, embodiments of the medical device and method are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A medical device for use in treating tissue in a mammalian body comprising a needle-like member having a distal portion adapted for introduction into the tissue of the body, plurality of laser diodes mounted on the distal portion of the needle-like member and extending helically around the needle-like member, and first and second electrical leads carried by the needle-like member for providing electrical energy to the at least one of the laser diodes.

2. The medical device of claim 1 wherein the needle-like member is a metal needle.

3. The medical device of claim 1 wherein the plurality of laser diodes extend along a length of the needle-like member.

4. A method for treating cancerous tissue in a mammalian body with porfimer sodium and a medical probe having a distal portion comprising the steps of introducing porfimer sodium into the body, introducing the medical probe into the body so that the distal portion is in the vicinity of the cancerous tissue and supplying light from the distal portion of the medical probe to activate the porfimer sodium in the vicinity of the cancerous tissue, wherein the step of introducing porfimer sodium into the body includes the step of injecting the porfimer sodium into the body in the vicinity of the cancerous tissue, wherein the injecting step includes the step of introducing a needle into the body and supplying the porfimer sodium through the needle to the cancerous tissue, wherein the distal portion of the probe includes a needle-like member having an exterior surface and at least one light source mounted on the exterior surface, and wherein the step of supplying light from the distal portion of the medical probe comprises supply light from the at least one light source.

5. A method for treating cancerous tissue in a mammalian body, the method comprising:

introducing into the body a photosensitizing agent that in response to absorbing light creates or increases an activity to destroy or inhibit cancerous tissue;

introducing a medical probe having a distal portion into the body such that the distal portion is in the vicinity of the cancerous tissue; and supplying light from the distal portion of the medical probe to activate the photosensitizing agent to destroy or inhibit cancerous tissue, wherein the cancerous tissue is located in a prostate, and the step of introducing a medical probe having a distal portion into the body such that the distal portion is in the vicinity of the cancerous tissue includes:

introducing the distal portion of a medical probe into the urethra; and advancing a needle from the distal portion through the wall of the urethra into the prostate in the vicinity of the cancerous tissue, and wherein the step of supplying light from the distal portion of the medical probe comprises supplying light from the needle.

6. The method of claim 5 in which the activity of the photosensitizing agent created or increased in response to absorbing light is selected from a group comprising:
   emitting energy;
   emitting energy at a different wavelength than the absorbed light;
   inducing a photochemical effect;
   inducing a thermal effect; and
   eliciting a necrotic reaction and associated inflammatory response.

7. The method of claim 5 in which the photosensitizing agent comprises a mixture of oligomers formed by ether and ester linkages of up to eight porphyrin units.

8. The method of claim 5 in which the photosensitizing agent comprises porfimer sodium.

9. The method of claim 5 in which the step of introducing into the body a photosensitizing agent that absorbs light and emits sufficient energy to destroy or inhibit cancer cells includes:
   intravenously administering the photosensitizing agent.

10. The method of claim 5 in which the step of introducing into the body a photosensitizing agent that absorbs light and emits sufficient energy to destroy or inhibit cancer cells includes:
    injecting the photosensitizing agent in the vicinity of the cancerous tissue.

11. The method of claim 5 in which the step of supplying light from the needle to activate the photosensitizing agent so that it emits sufficient energy to destroy or inhibit cancerous tissue includes:
    activating at least one laser diode located along the needle.

12. A medical device for photodynamically treating prostate cancer comprising:
    a generally cylindrical body sized and configured for introduction into the urethra of a patient;
    a needle movable between a retracted position housed substantially within the cylindrical body, and a deployed position in which the needle extends from the cylindrical body to enable it to penetrate into prostate tissue; and
    at least one light-emitting diode mounted on the needle adapted to emit light to activate a photosensitizing agent in or adjacent cancerous tissue in the prostate.

13. The medical device of claim 12 in which the at least one light-emitting diode comprises a laser diode.

14. The medical device of claim 12 in which the at least one light-emitting diode comprises a plurality of light-emitting diode, the diodes being arranged along a flex circuit.

15. The medical device of claim 12 in which the needle is made of material that is able to flex as the needle is moved between the retracted and deployed positions.

16. The medical device of claim 12 wherein the needle is a metal needle.

17. The medical device of claim 12 wherein the at least one light-emitting diode includes a plurality of laser diodes extending along a length of the needle.

18. The medical device of claim 12 wherein the at least one light-emitting diode includes a plurality of laser diodes extending helically around the needle.

19. The medical device of claim 12 in which the needle, when in its deployed position, extends laterally from the body.

20. The medical device of claim 12 in which the needle comprises a plurality of needles deployed at different locations along the length or circumference of the body.

* * * * *